(12) United States Patent
Bombardelli et al.

(10) Patent No.: US 6,656,510 B2
(45) Date of Patent: Dec. 2, 2003

(54) HYPERFORIN DERIVATIVES, USE THEREOF AND FORMULATIONS CONTAINING THEM

(75) Inventors: Ezio Bombardelli, Milan (IT); Paolo Morazzoni, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/730,536

(22) Filed: Dec. 7, 2000

(65) Prior Publication Data

US 2001/0020040 A1 Sep. 6, 2001

Related U.S. Application Data

(63) Continuation of application No. PCT/EP99/03880, filed on Jun. 4, 1999.

(30) Foreign Application Priority Data

Jun. 10, 1998 (IT) .......................................... MI98A1312

(51) Int. Cl.$^7$ ........................ A61K 35/78; A61K 31/05
(52) U.S. Cl. ...................................... 424/730; 514/732
(58) Field of Search ........................... 514/732; 424/730

(56) References Cited

U.S. PATENT DOCUMENTS 2,550,266 A * 4/1951 Jensen et al.
6,224,906 B1 * 5/2001 Ghosal
6,280,736 B1 * 8/2001 Erdelmeier et al.

FOREIGN PATENT DOCUMENTS

DE  WO 97 13489 A   4/1997
EP  0 599 307 A     6/1994

OTHER PUBLICATIONS

Bystrov et al. Bioorg. Khim. 1978. vol. 4, No. 6, pp. 791–797—English translation enclosed.*
Brondz et al. Acta Chem. Scandinnavica Series A. 1983. vol. 37, No. 3, pp. 263–265.*
Decosterd et al. Helvetica Chim. Acta. 1989. vol. 72, No. 3, pp. 464–471.*
Erdelmeier, C. Pharmacopsychiatry. Jun. 1998. vol. 31, Suppl. 1, pp. 2–6.*
Brondz, Ilia et al; "The relative stereochemistry of hyperforin" Tetrahedron Letters, vol. 23, No. 12, 1982 (pp. 1299–1300) XP002117275 Great Britian.

* cited by examiner

*Primary Examiner*—Christopher R. Tate
(74) *Attorney, Agent, or Firm*—Pennie & Edmonds LLP

(57) ABSTRACT

The invention relates to compounds of the formula:

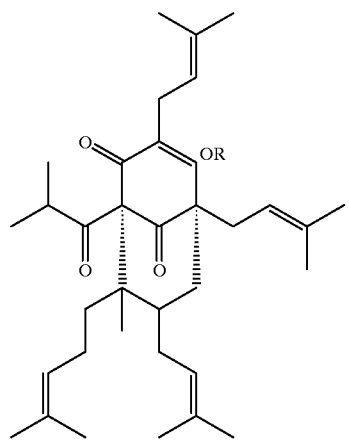

in which R is a saturated or unsaturated, straight or branched, $C_1$–$C_{22}$ acyl group, optionally having one or more substituents, which can be the same or different, selected from halogen atoms, nitro, amino, $C_1$–$C_6$-alkylamino, di-$C_1$–$C_6$-alkylamino, $C_1$–$C_6$-acylamino groups; a cycloaliphatic or aromatic acyl residue in which the aromatic moiety optionally has one or more substituents, which can be the same or different, selected from halogen atoms, hydroxy, methoxy, amino groups; a glycidic residue in which one or more hydroxy groups are optionally alkylated or acylated. The invention further relates to methods for extracting and extracts of these compounds from *Hypericum perforatum* as well as their use as active ingredients in antidepression medication.

10 Claims, No Drawings

HYPERFORIN DERIVATIVES, USE THEREOF AND FORMULATIONS CONTAINING THEM

CROSS-REFERENCE TO RELATED APPLICATIONS

This application is a continuation of the U.S. national stage designation of International Application No. PCT/EP99/03880, filed Jun. 4, 1999, the content of which is expressly incorporated herein by reference thereto.

TECHNICAL FIELD

The present invention relates to novel hyperforin derivatives, the use of such derivatives for the treatment of depression and anxiety, and to formulations containing them.

BACKGROUND OF THE INVENTION

Flowering tops of *Hypericum perforatum* contain a number of classes of structurally different substances that act directly or indirectly on the central nervous system. In particular, these compounds include hypericin, hyperforin, and dimeric flavones that exert antidepressive and anxiolycic activities on animals and humans. The mechanisms of action of these compounds are different and include anti-MAO action, action on serotonin release, and benzodiazepine-like activity. Hyperforin is one of the main components of the lipophilic fraction of *Hypericum perforatum* flowering tops and has recently been the subject of numerous studies that establish its important role as an antidepressant. Applicant has discovered that this molecule has serotoninmimetic activity.

Hyperforin is not very stable to typical extraction and storage conditions. WO 97/13489 to Schwabe shows that the hyperforin content of a water-alcohol extract of St. Johns wort falls almost to zero after only a few weeks. WO 97/13489 further recites that in order to obtain stable extracts with a constant hyperforin content, extraction, purification, and storage should be carried out in the presence of antioxidants such as vitamin C and the esters thereof, sulfated amino acids, and the like. The high instability of hyperforin makes the preparation of hyperforin formulations rather difficult.

SUMMARY OF THE INVENTION

The invention relates to a compound having the formula:

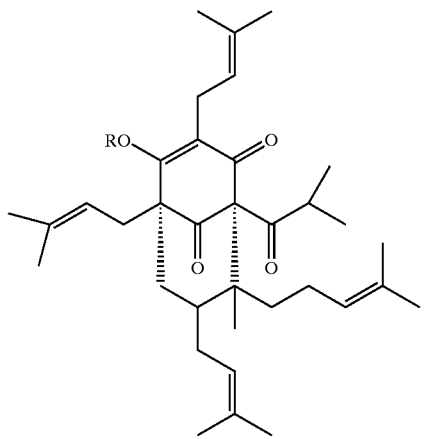

wherein R is a saturated or unsaturated, straight or branched, $C_1$–$C_{22}$ acyl group, optionally having one or more substituents, which can be the same or different, selected from a group consisting of halogen atoms, nitro, amino, $C_1$–$C_6$-alkylamino, di-$C_1$–$C_6$-alkylamino, and $C_1$–$C_6$-acylamino groups; a cycloaliphatic or aromatic acyl residue wherein the aromatic moiety optionally has one or more substituents, which can be the same or different, selected from the group consisting of halogen atoms, hydroxy, methoxy, and amino groups; or a glycidic residue wherein one or more hydroxy groups are optionally alkylated or acylated. The invention also relates to an extract of *Hypericum perforatum* containing this compound.

The invention further relates to a process for preparing extracts including the compound of formula I. The method involves extracting *Hypericum perforatum* flowering tops with supercritical $CO_2$ to obtain a lipophilic extract; dissolving the lipophilic extract in aqueous methanol or acetonitrile to form a hydrophilic phase; extracting the hydrophilic phase with aliphatic hydrocarbons to provide a first aliphatic hydrocarbon phase; diluting the hydrophilic phase with water and counter-extracting the phase with aliphatic hydrocarbons to provide a second aliphatic hydrocarbon phase; combining the first and second aliphatic hydrocarbon phases; concentrating the combined first and second aliphatic hydrocarbon phases; treating the concentrate with a reactive derivative of a RCOOH acid or of an ROH sugar, wherein R is a saturated or unsaturated, straight or branched, $C_1$–$C_{22}$ acyl group, optionally having one or more substituents, which can be the same or different, selected from the group consisting of halogen atoms, nitro, amino, $C_1$–$C_6$-alkylamino, di-$C_1$–$C_6$-alkylamino, and $C_1$–$C_6$-acylamino groups; a cycloaliphatic or aromatic acyl residue in which the aromatic moiety optionally has one or more substituents, which can be the same or different, selected from the group consisting of halogen atoms, hydroxy, methoxy, and amino groups; or a glycidic residue wherein one or more hydroxy groups are optionally alkylated or acylated.

The invention also relates to a pharmaceutical composition including the compound of formula I and a pharmaceutically acceptable carrier or extract. This pharmaceutical composition is further formulated as a soft-gelatin capsule, hard-gelatin capsule, tablet, or suppository. In a preferred embodiment, the composition includes from 5 to 50 mg of the compound. The pharmaceutical composition can also be formulated as a controlled release dosage form. In a preferred embodiment, the composition includes up to 200 mg of the compound.

The invention also relates to a method of treating depression in an animal including administering to an animal the compound of formula I and extracts thereof.

DETAILED DESCRIPTION OF THE INVENTION

New hyperforin derivatives have been discovered that are stable and more active as antidepressants. The derivatives of the invention have the following formula:

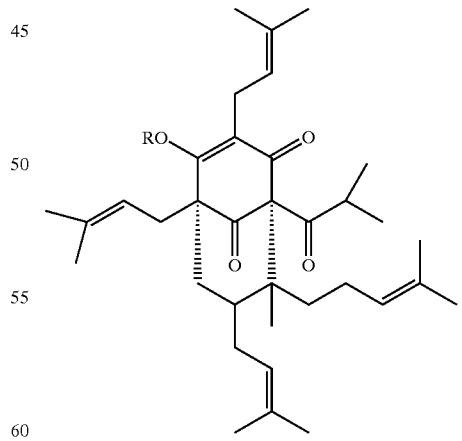

wherein R is:
 a saturated or unsaturated, straight or branched, $C_1$–$C_{22}$ acyl group, optionally having one or more substituents, which can be the same or different, selected from halogen atoms, nitro, amino, $C_1$–$C_6$-alkylamino, di-$C_1$–$C_6$-alkylamino, $C_1$–$C_6$-acylamino groups;

a cycloaliphatic or aromatic acyl residue in which the aromatic moiety has optionally one or more substituents, which can be the same or different, selected from halogen atoms, hydroxy, methoxy, amino groups;

a glycidic residue in which one or more hydroxy groups are optionally alkylated or acylated.

Preferably the "aromatic acyl residue" is a benzoyl or cinnamyl residue having one or more amino or alkoxy groups.

Preferably the "glycidic residue" is a residue of one sugar bound by an ether bond to the hydroxy group at the 1-position of the pyranosyl or furanosyl ring, with the other hydroxy groups of the sugar optionally methylated or acetylated.

Preferably R is acetyl, monochloroacetyl, butyryl, γ-aminobutyryl, p-aminobenzyl, trimethoxybenxyl, trimethoxycinnamyl, β-glucosyl, or β-galactosyl.

The hyperforin derivatives of the invention can be prepared with conventional methods, well know to those of ordinary skill in the art, for acylation or glycosylation of hydroxy groups. For example, hyperforin, either as substantially pure or as an extract enriched in hyperforin, can be subjected to a reaction with acid chlorides or anhydrides of RCOOH acids ® as defined above) in suitable solvents, such as pyridine.

Glycosylations can be carried out using a suitably protected reactive derivative of the desired sugar (ROH), for example α-D-glucopyranosyl bromide tetraacetate.

A particularly convenient aspect of the invention is that the compounds of formula I can be prepared by extracting *Hypericum perforatum* flowering tops with carbon dioxide under supercritical conditions, subsequently partitioning the extract between solvents, and derivatizing hyperforin in the resulting extract.

Leaves and flowering tops of St. Johns wort, separately or in mixtures, preferably as natural mixtures, are extracted with carbon dioxide in supercritical conditions under pressures of 180 to 260 bars, preferably about 240 bars, and at temperatures of 35° C. to 50° C., preferably 40° C. A lipophilic extract is obtained containing about 50% hyperforin and considerable amounts of xanthones, waxes, fatty acids, and triglycerides. The hyperforin percentage is subsequently increased by dissolving the resulting extract in methanol or in partially aqueous acetonitrile and then extracting the solution with n-hexane or aliphatic hydrocarbons. The hydrocarbon phase also contains undesirable substances which are removed. The hydrophilic phase is then diluted with about equal volumes of water and aliphatic hydrocarbons and the hydrocarbon layers are combined. The extract of St. Johns wort obtained by concentration of the hydrocarbon phase can be used for the preparation of the derivatives as described above.

The derivatives of the invention exert no activity in vitro on receptors, but are particularly active in vivo, exerting strong antidepressive activity that is related to the dosage. In an in vivo test in mice and rats, the compounds of the invention showed a higher activity than hyperforin and Hypericum ethanol or methanol extracts. The escape deficit development test and the inhibition of the ethanol consumption in Sardinia alcohol preferring rats, according to models known in literature, were selected as in vivo tests to verify the antidepressive effect.

In the escape deficit development test, the compounds of the invention showed a higher activity than known extracts and an activity comparable with that of known medicaments such as imipramine. In the escape deficit development test, rats are restrained and subjected to mild, short, unavoidable electric shocks for 50 minutes. This is known as the pre-test. 24 hours later, the rats are tested for their ability to avoid the same stimuli on their tails, in a situation where escape is impossible. A rat on the average makes 26 escapes out of 30 stimuli (naive controls), whereas a rat subjected to pre-test only makes 1 to 3 escapes (ED controls). The reduction in reactivity induced by the pre-test does not take place in rats that are pre-treated for 1 to 3 weeks with antidepressants such as imipramine or fluoxetine. The compounds of the invention, when administered to rats one hour before their exposure to the unavoidable stress, cause an increase in reactivity to the escape test. This increase in reactivity is enhanced when pre-treatment is effected for 1 to 2 weeks.

For example, treatment of rats with a compound of Formula I in which R is acetyl yields the results reported in the following Table:

Antidepressive effect of the acetate derivative of Hyperforin in rats in the escape test deficit development with a 2 week pre-treatment.

| Substance | Dosage (mg/Kg) | Number of Escapes |
| --- | --- | --- |
| Hyperforin acetate | 6.25 | 12.6 ± 2.8 |
| Hyperforin acetate | 12.5 | 17.3 ± 1.9 |
| Hyperforin acetate | 25.0 | 21.2 ± 1.3 |
| Hyperico alcoholic extract | 1000 | 15.6 ± 2.4 |
| Hyperico hexane extract | 600 | 16.9 ± 1.2 |
| ED controls | | 2.6 ± 0.7 |
| Naive controls | | 23.6 ± 1.2 |

Statistical analysis: Kruskal-Wallis non parametric
ANOVA KW=13.462 p 0.0012
Hypericum alcoholic extract and
hexane extract vs naive p<0.01
Hyperforin acetate 25 mg vs naive n.s.
Naive vs AND p<0.01

In a test of the reduction of alcohol consumption (which is an index of depression and anxiety) in Sardinia rats according to procedures known in literature, the compounds of the invention, after a two-day administration, induced a 60% to 75% decrease in alcohol consumption in favor of water compared with controls.

The compounds of Formula I can be formulated in soft-gelatin capsules, hard-gelatin capsules, tablets, or suppositories. Preferably the compounds of the invention are formulated in soft-gelatin capsules or in controlled-release formulations. The dosages of compounds in the formulations are 5 to 50 mg per dose in the usual formulations and up to 200 mg in the controlled-release formulations. The preferred dosage in the controlled-release formulations is 200 mg per dose daily.

EXAMPLES

The following examples illustrate the invention in greater detail and are presented for illustrative purposes and are not meant to limit the invention in any way.

Example 1

Preparation of a Hyperforin-enriched Extract 10 kg of biomass of *Hypericum perforatum* was extracted in a 25 L extraction apparatus for supercritical gas, equipped with two separators, according to the following procedure:

The 10 kg of *Hypericum perforatum* flowering tops was mechanically dried, after collecting, at a temperature not exceeding 60° C. The dried flowering tops were extruded into cubes to break the cells and then extracted with $CO_2$ under supercritical conditions with the following experimental conditions:

temperature: 45° C. in the extractor, 30° C. in the first separator, and 20° C. in the second separator;

pressure: 240 bars in the extractor, 100 bars in the first separator, and 50 bars in the second separator.

The $CO_2$ flow was 10 liters per minute for 45 minutes. The extract was concentrated in the second separator, whereas most water present in the vegetable matrix was concentrated in the first separator. The extract present in the second separator was dissolved in 3.2 liters of methanol and the resulting solution extracted with 3×1.5 liters of n-hexane. The hexane phase was then counter-washed with 98% methanol. The hexane phase was then removed and the methanolic phases diluted with 0.6 liters of water and re-extracted with 2×0.6 liters of n-hexane. The combined hexane phases were decolorized with 0.3% charcoal, dried ($Na_2SO_4$), and then concentrated to an oil under vacuum pressure at a temperature not exceeding 40° C. About 0.22 kg of a waxy extract was obtained, having a hyperforin content of about 70%.

Example 2

Synthesis of Hyperforin Acetate

A solution of 12 g of the plant extract obtained in Example 1 in 48 mL of pyridine was added to 9.8 mL of $Ac_2O$ and stirred at room temperature. The reaction was monitored by thin layer chromatography (TLC) (hexane-EtOAc 95:5; hyperforin Rf: 0.24; acetate Rf: 0.49). After 24 hours, the reaction mixture was diluted with water and extracted with a 3:1 hexane-ether mixture. The organic phase was washed with dilute HCl, saturated $NaHCO_3$, and saline solution. After drying ($Na_2SO_4$) and evaporation, the residue was purified by chromatography on a silica gel column (ca 30 g), eluted first with petroleum ether to remove fats, then using hexane-EtOAc 95:5 as soon as the title compound started to elute. Hyperforin acetate (3.34 g, 0.28%) was obtained as a colorless paste with the following properties:

Formula: $C_{37}H_{54}O_5$
Molecular Weight: 578
CI-MS: 579 (M+H)+
IR (liquid film): 1779, 1732, 1660, 1634, 1447, 1377, 1339, 1146 $cm^{-1}$
$^1$H NMR (200 MHZ, $CDCl_3$): 5.03 (br s, 2H), 5.00 (br s, 2H), 3.05 (dd, J=15, 7 Hz, 1H), 2.87 (dd, J=15, 7 Hz, 1H), 2.22 (s, OAc), 1.66–1.53 (br s, 8×3H), 1.08 (d, J=6.5 Hz, 3H), 0.98 (s, 3H), 0.85 (d, J=6.5 Hz, 3H).

Example 3

Synthesis of Hyperforin 3,4,5-trimethoxybenzoate

A solution of 1.0 g of the plant extract of Example 1 in 4 mL pyridine was added to 323 mg of 3,4,5-trimethoxybenzoyl chloride and the solution was stirred at room temperature for 24 hours. The reaction could not be monitored by TLC, as the starting material and the product have similar Rf values in different solvents. The reaction mixture was diluted with water and extracted with a 3:1 ether-hexane mixture. The organic phase was washed with dilute HCl and saturated $NaHCO_3$ (washing with saline solution causes an emulsion to form). After drying ($Na_2SO_4$) and evaporation, the residue was purified by chromatography on a silica gel column (ca 5 g), and eluted first with petroleum ether to remove fats, then with hexane-EtOAc 95:5 to obtain hyperforin trimethoxybenzoate (317 mg) as a colorless oil with the following properties:

Formula: $C_{45}H_{62}O_8$
Molecular Weight: 730
CI-MS: 731 (M+H)+
IR (liquid film): 1732, 1660, 1634, 1589, 1465, 1331, 1153, 1130, 914 $cm^{-1}$
$^1$H NMR (200 MHZ, $CDCl_3$): 7.27 (s, 2H), 5.04 (br s, 2H), 5.02 (br s, 2H), 3.86 (s, OMe), 3.82 (s, 2×OMe), 3.10 (dd, J=15, 7 Hz, 1H), 2.92 (dd, J=15, 7 Hz, 1H), 1.66–1.53 (br s, 8×3H), 1.13 (d, J=6, 5 Hz, 3H), 1.04 (s,3H), 0.99 (d, J=6.5 Hz, 3H).

Example 4

Coated Tablets Containing the Product of Example 2

Hyperforin acetate 100 mg
Soy polysaccharides 18.25 mg
Cross-linked sodium carboxymethylcellulose 13.50 mg
Silica 6.50 mg
Polyvinylpyrrolidone 5.00 mg
Magnesium stearate 0.50 mg
Coating:
Hydroxypropyl methylcellulose 3.75 mg
Talc 2.75 mg
Titanium dioxide 1.25 mg
Triacetin 0.75 mg
Polysorbate 80 0.25 mg
Red iron oxide 1.00 mg

What is claimed is:

1. A compound having the formula:

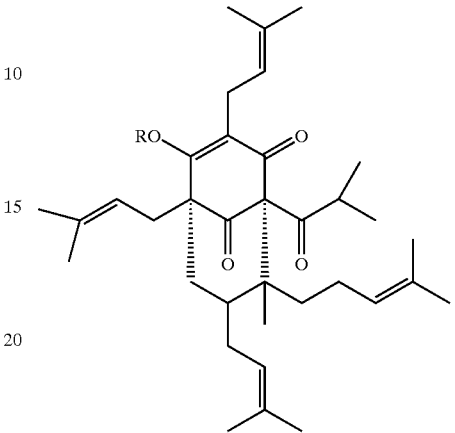

wherein R is:
a cycloaliphatic or aromatic carbonyl residue wherein the aromatic moiety optionally has one or more substituents, which can be the same or different, selected from the group consisting of hydroxy, methoxy, and amino groups.

2. The compound of claim 1 wherein R is selected from the group consisting of p-aminobenzyl, trimethoxybenxyl, or trimethoxycinnamyl.

3. A method of treating depression in an animal, comprising administering to an animal in need of such treatment the compound of claim 1.

4. A method of treating depression in an animal, comprising administering to an animal in need of such treatment the compound of claim 2.

5. A pharmaceutical composition comprising a compound of the formula:

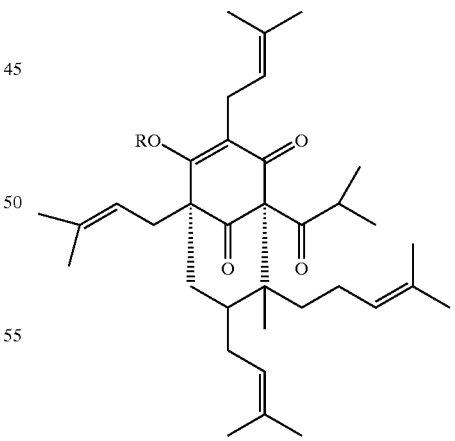

wherein R is:
a cycloaliphatic or aromatic carbonyl residue wherein the aromatic moiety optionally has one or more substituents, which can be the same or different, selected from the group consisting of hydroxy, methoxy, and amino groups;
and a pharmaceutically acceptable carrier.

6. The pharmaceutical composition of claim 1, wherein R is selected from the group consisting of acetyl, monochloroacetyl, butyryl, γ-aminobutyryl, p-aminobenzyl, trimethoxybenxyl, trimethoxycinnamyl, β-glucoside, and β-galactosyl.

7. The pharmaceutical composition of claim 1 formulated as a soft-gelatin capsule, hard-gelatin capsules, tablet, or suppository.

8. The pharmaceutical composition of claim 7, comprising from 5 to 50 mg of the compound.

9. The pharmaceutical composition of claim 1 formulated as a controlled release dosage form.

10. The pharmaceutical composition of claim 9, comprising up to 200 mg of the compound.

* * * * *

UNITED STATES PATENT AND TRADEMARK OFFICE
CERTIFICATE OF CORRECTION

PATENT NO. : 6,656,510 B1
DATED : December 2, 2003
INVENTOR(S) : Ezio Bombardelli and Paolo Morazzoni It is certified that error appears in the above-identified patent and that said Letters Patent is hereby corrected as shown below:

<u>Column 6,</u>
Lines 32-33, replace "p-aminobenzyl, trimethoxybenxyl, and trimethoxycinnamyl" with -- p-aminobenzoyl, trimethoxbenzoyl, and trimethoxycinnamoyl --

<u>Column 7,</u>
Lines 3-4, replace "p-aminobenzyl, trimethoxybenxyl, trimethoxycinnamyl, $\beta$-glucoside" with -- p-aminobenzoyl, trimethoxybenzoyl, trimethoxycinnamoyl, $\beta$-glucosyl --.

Signed and Sealed this

Seventeenth Day of February, 2004

JON W. DUDAS
*Acting Director of the United States Patent and Trademark Office*